United States Patent [19]

Wedemeyer et al.

[11] Patent Number: 4,460,788

[45] Date of Patent: Jul. 17, 1984

[54] PROCESS FOR PREPARATION OF ANILINES WHICH ARE M-SUBSTITUTED BY CHLORINE

[75] Inventors: Karlfried Wedemeyer, Cologne; Ferdinand Hagedorn, Leverkusen; Werner Evertz, Monheim, all of Fed. Rep. of Germany

[73] Assignee: Bayer Aktiengesellschaft, Leverkusen, Fed. Rep. of Germany

[21] Appl. No.: 389,127

[22] Filed: Jun. 16, 1982

[30] Foreign Application Priority Data

Jul. 9, 1981 [DE] Fed. Rep. of Germany ....... 3127026

[51] Int. Cl.$^3$ ..................... C07C 85/24; C07C 87/60
[52] U.S. Cl. ..................................................... 564/412
[58] Field of Search ........................................ 564/412

[56] References Cited

U.S. PATENT DOCUMENTS

| 3,888,929 | 6/1975 | Rivier | 564/412 |
|---|---|---|---|
| 4,193,937 | 3/1980 | Wedemeyer et al. | 564/412 |
| 4,206,147 | 6/1980 | Daumas et al. | 564/412 |
| 4,206,148 | 6/1980 | Biola et al. | 564/412 |
| 4,324,914 | 4/1982 | Cordier | 564/412 |
| 4,340,759 | 7/1982 | Cordier | 564/412 |
| 4,351,959 | 9/1982 | Cordier | 564/412 |

FOREIGN PATENT DOCUMENTS

| 2258769 | 6/1973 | Fed. Rep. of Germany | 564/412 |
|---|---|---|---|
| 2503145 | 7/1976 | Fed. Rep. of Germany | 564/412 |
| 2503187 | 7/1976 | Fed. Rep. of Germany | 564/412 |
| 3042242 | 6/1982 | Fed. Rep. of Germany | . |
| 2041375 | 9/1980 | United Kingdom | 564/412 |

*Primary Examiner*—Thomas A. Waltz
*Attorney, Agent, or Firm*—Sprung, Horn, Kramer & Woods

[57] ABSTRACT

The invention relates to a process for the preparation of anilines which are m-substituted by chlorine, by selective dehalogenation of more highly chlorinated anilines in an acid medium in the presence of noble metal catalysts and in the presence of optionally substituted phenols.

The 3-chloro- or 3,5-dichloroanilines obtainable by the process according to the invention are known intermediate products, and can be used for the preparation of plant protection agents.

10 Claims, No Drawings

PROCESS FOR PREPARATION OF ANILINES WHICH ARE M-SUBSTITUTED BY CHLORINE

The invention relates to a process for the preparation of anilines which are m-substituted by chlorine, by selective dehalogenation of more highly chlorinated anilines.

The preparation of anilines, which are m-substituted by chlorine, by selective dehalogenation of more highly halogenated anilines in solution in an acid medium in the presence of noble metal catalysts and, if appropriate, in the presence of sulphur and/or sulphur compounds has been disclosed in German Patent Specification No. 2,503,145 and German Patent Specification No. 2,503,187.

The processes described in German Patent Specification No. 2,503,145 and German Patent Specification No. 2,503,187, however, can be carried out economically only at high temperatures and pressures, that is to say at temperatures of above 200° C. and pressures of above 60 bar (in this context, see also the examples of the patent specifications mentioned). Since the high reaction temperatures and pressures used in these processes place a particularly high stress, for example, on the container materials, these processes are difficult to carry out industrially.

The preparation of anilines, which are m-substituted by halogen, by dehalogenating halogen-substituted anilines under conditions of hydrogenation, using noble metal catalysts, in the presence of hydrogen iodide and simultaneously in the presence of optionally substituted phenols is also known (German patent application No. P 3 042 242.5).

Furthermore, German Offenlegungsschrift No. 3,003,960 discloses a process for the preparation of anilines which are m-substituted by chlorine, in which the dehalogenation under conditions of hydrogenation is carried out in the presence of a greatly increased chloride ion concentration. This process has the disadvantage that only low concentrations of the compound employed for dehalogenation can be used in solutions with a relatively high chloride ion concentration, resulting in poor space/time yields and an increased corrosion of the apparatus. From the only example of this application, it is to be presumed that good results are achieved only in the presence of lithium chloride. In this procedure, however, large amounts of non-separable salt mixtures are obtained, the working-up and elimination of which present particular ecological problems.

In European Patent Application No. 0,015,219, a process is claimed in which the dehalogenation under conditions of catalytic hydrogenation is carried out in the presence of iodide or bromide ions. This process has the disadvantage that still larger amounts of hydrochloric acid have to be added in addition to the hydrogen chloride formed during the reaction, whereby, on the one hand, the amount of hydrogen chloride inevitably produced, or the salt formed therefrom by neutralisation, is increased, and on the other hand, the danger of corrosion of the apparatus used is increased. A further substantial disadvantage is that only low concentrations of the compound employed for dehalogenation can be used in the reaction mixture (see Examples 1 to 15: maximum 3% by weight). However, if it is required to dehalogenate larger amounts of starting material, it is necessary to employ a larger amount of catalyst, based on the compound to be dehalogenated (see Example 16; concentration of tetrachloronitrobenzene in the mixture: 12%, amount of catalyst: 57% by weight, based on tetrachloronitrobenzene). The use of iodide or bromide compounds in this process makes it necessary, for ecological and economic reasons, to separate these compounds from the reaction mixture and to recover them by a working-up procedure, thus making it difficult to put the process into practice.

As may be seen from the above arguments, the process described in European Patent Application 0,015,219 is not very suitable industrially and economically.

A process for the preparation of anilines, which are m-substituted by chlorine, by the reaction of anilines of the formula (I)

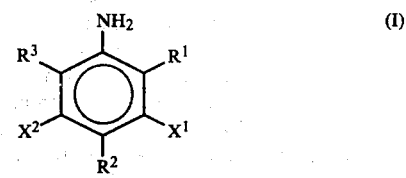

wherein $X^1$ and $X^2$ are identical or different and represent chlorine, hydrogen or an optionally substituted alkyl, aryl, aralkyl, alkoxy or aralkoxy radical, one of the radicals $X^1$ or $X^2$ representing chlorine in the preparation of 3-chloroanilines, and $X^1$ and $X^2$ representing chlorine in the preparation of 3,5-dichloroaniline; and $R^1$, $R^2$ and $R^3$ are identical or different and represent chlorine, hydrogen or an optionally substituted alkyl, aryl, aralkyl, alkoxy or aryloxy radical, at least one of the radicals $R^1$, $R^2$ or $R^3$ representing chlorine, with hydrogen in an acid medium in the presence of noble metals, in elementary or bonded form, which may be applied onto carriers, and if appropriate in the presence of inert, organic solvents and/or diluents and/or water, at an elevated temperature and elevated pressures has now been found, which is characterized in that the reaction is carried out in the presence of optionally substituted phenols.

By the process according to the invention anilines which are m-substituted by chlorine, of the formula (II)

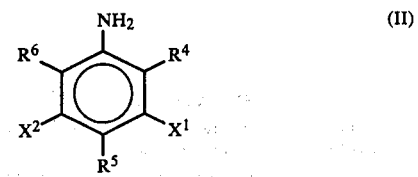

wherein $X^1$ and $X^2$ have the meaning given above, and $R^4$, $R^5$ and $R^6$ are identical or different and represent hydrogen or an optionally substituted alkyl, aryl, aralkyl, alkoxy or aryloxy radical, are obtained.

Optionally substituted aliphatic radicals ($R^1$, $R^2$, $R^3$, $R^4$, $R^5$ and $R^6$) can, for example, be straight-chain or branched aliphatic radicals, e.g. alkyl radicals, having 1 to 12, preferably 1 to 6, carbon atoms, and cycloaliphatic radicals, e.g. cycloylkyl radicals, having 5 to 8, preferably 5 and 6, carbon atoms in the ring. The methyl, the ethyl, the propyl, the isopropyl, the butyl, the pentyl, the hexyl, the octyl, the nonyl, the decyl, the dodecyl, the cyclopentyl, the cyclohexyl, the cycloheptyl and the cyclooctyl radical be mentioned as examples.

Optionally substituted aromatic radicals ($R^1$, $R^2$, $R^3$, $R^4$, $R^5$ and $R^6$) can be radicals from the benzene series, preferably the phenyl or the naphthyl radical.

Optionally substituted aralkyl radicals ($R^1$, $R^2$, $R^3$, $R^4$, $R^5$ and $R^6$) can, for example, be those having 7 to 18 carbon atoms, the aliphatic part of which contains 1 to 6 carbon atoms, preferably 1 to 3 carbon atoms, and the aromatic part of which represents a radical from the benzene series, preferably the phenyl or the naphthyl radical. The following aralkyl radicals may be mentioned as examples: the benzyl, the β-phenyl-ethyl, the α-phenyl-propyl, the β-phenyl-n-hexyl, the β-(Naphthyl-(1))-ethyl, the ω-butyl-phenyl, the ω-pentyl-phenyl and the ω-hexyl-phenyl radical.

Optionally substituted alkoxy radicals ($R^1$, $R^2$, $R^3$, $R^4$, $R^5$ and $R^6$) can be straight-chain and branched radicals having 1 to 12, preferably 1 to 6, carbon atoms, as well as cycloaliphatic radicals, e.g. cycloalkyl radicals, having 5 and 6 carbon atoms in the ring. The methoxy, the ethoxy, the propoxy, the isopropoxy, the butoxy, the tert.-butoxy, the pentoxy, the hexoxy, the octoxy, the nonoxy, the decoxy, the dodecoxy, the cyclopentoxy and the cyclohexoxy radical may be mentioned as examples.

Optionally substituted aryloxy radicals ($R^1$, $R^2$, $R^3$, $R^4$, $R^5$ and $R^6$) which may be mentioned are radicals from the benzene series, preferably the phenoxy radical.

Examples of suitable substituents of the alkyl, aryl, aralkyl, alkoxy or aralkoxy radicals listed above are the amino group, the hydroxyl group, straight-chain or branched alkyl radicals having up to 12, preferably up to 6, carbon atoms, cycloaliphatic radicals preferably having 5 and 6 carbon atoms in the ring, and aryl radicals, preferably the phenyl radical.

Particularly preferred chloroanilines which can be employed in the process according to the invention are compounds of the formula (III)

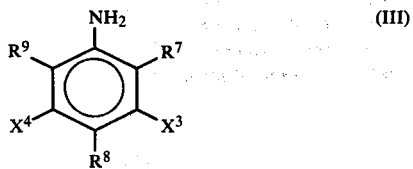

(III)

wherein $X^3$ and $X^4$ are identical or different and represent chlorine or hydrogen, one of the radicals $X^3$ or $X^4$ representing chlorine in the preparation of 3-chloroanilines, and $X^3$ and $X^4$ representing chlorine in the preparation of 3,5-dichloroanilines, $R^7$, $R^8$ and $R^9$ are identical or different and represent hydrogen, the methyl group or the phenyl group, or the radical

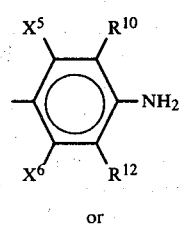

or

-continued

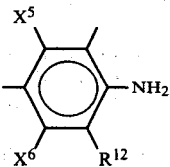

wherein $X^5$ and $X^6$ are identical or different and represent chlorine or hydrogen, and $R^{10}$, $R^{11}$ and $R^{12}$ are identical or different and represent chlorine, hydrogen, the methyl group or the phenyl group, at least one of the radicals $R^7$, $R^8$ or $R^9$ representing chlorine.

The polychloroanilines of the formula (I), which can be used in the process according to the invention, are known and are readily obtainable.

The following may be mentioned as examples: 2,3-dichloroaniline, 2,5-dichloroaniline, 3,4-dichloroaniline, 2,3,4-trichloroaniline, 2,3,5-trichloroaniline, 2,4,5-trichloroaniline, 2,3,6-trichloroaniline, 3,4,5-trichloroaniline, 2,3,4,6-tetrachloroaniline, 2,3,4,5-tetrachloroaniline, 2,3,5,6-tetrachloroaniline, pentachloroaniline, 4,5,6-trichloro-2-methylaniline, 2,5-dichloro-4-methylaniline, 2,3,5,6-tetrachloro-4-methylaniline, 2,5-dichloro-3,4-dimethylaniline, 2,5-dichloro-4-ethylaniline, 2,5-dichloro-4-propylaniline, 3,4,6-trichloro-2-benzylaniline, 2,2'-diamino-3,5,6,3',5',6'-hexachlorodiphenylmethane, 3,4,5-trichloro-2-aminodiphenyl, 4,4'-diamino-octachlorodiphenyl, 3,4-dichloro-2-methoxyaniline, 3,6-dichloro-2-methoxyaniline, 4,5-dichloro-2-methoxyaniline, 5,6-dichloro-2-methoxyaniline, 3,4,6-trichloro-2-methoxyaniline, 3,4,5-trichloro-2-methoxyaniline, 3,4,5,6-tetrachloro-2-methoxyaniline, 4,5-dichloro-3-methoxyaniline, 5,6-dichloro-3-methoxyaniline, 2,5-dichloro-3-methoxyaniline, 4,5,6-trichloro-3-methoxyaniline, 2,4,5,6-tetrachloro-3-methoxyaniline, 2,3-dichloro-4-methoxyaniline, 2,5-dichloro-4-methoxyaniline, 2,3,6-trichloro-4-methoxyaniline, 2,3,5-trichloro-4-methoxyaniline, 2,3,5,6-tetrachloro-4-methoxyaniline, 4,5-dichloro-2-phenoxyaniline, 3,4,5,6-tetrachloro-2-phenoxyaniline, 2,4,5,6-tetrachloro-3-phenoxyaniline, 2,5-dichloro-4-phenoxyaniline, 2,3,5,6-tetrachloro-4-phenoxyaniline.

The process according to the invention is carried out in the presence of optionally substituted phenols as the reaction medium.

Suitable optionally substituted phenols are those which are monosubstituted or polysubstituted by alkyl groups having up to 4, preferably 1 to 3, carbon atoms, and/or by halogen, preferably by chlorine.

Examples which may be mentioned are: phenol, o-, m- and p-cresol, 2,3-, 2,4-, 2,5-, 2,6- and 3,5-xylenol, preferably phenol, o-, m- and p-cresol.

The optionally substituted phenols can be employed in the process according to the invention both individually and mixed with one another, for example m-cresol/p-cresol mixtures.

The amount of optionally substituted phenols to be employed in the process according to the invention can be varied within wide ranges. Customarily from 1 to 90% by weight, preferably from 30 to 70% by weight, of optionally substituted phenols, relative to the total weight of the reaction mixture, are employed in the process according to the invention.

The optionally substituted phenols are preferably employed undiluted in the process according to the invention. However it is also possible to employ the phenols in solution in, or diluted with, an organic solvent and/or diluent which is inert under the reaction conditions, or in water.

The elements of group 8 of the Periodic Table of Elements (Mendeleev), such as ruthenium, rhodium, palladium, osmium, iridium and platinum, preferably palladium and platinum, may be mentioned as noble metals.

The oxides, sulphides and/or polysulphides, for example, can be employed as the bonded form of the noble metals.

The catalysts according to the process according to the invention can also be used on carrier materials. All carrier materials which are in themselves known, provided they are inert to water and acids, are suitable for this purpose. Barium sulphate and active charcoal, preferably active charcoal, may be mentioned as such materials.

The preparation of the noble metal catalyst on a carrier material can be effected in a manner which is in itself known. For example, the carrier material is suspended in the aqueous solution of the noble metal, and the noble metal is then precipitated on to the carrier material by the addition of a reducing agent, such as hydrogen or hydrazine.

It is advantageous to arrange the noble metal catalyst on a carrier material in the reaction space as a fixed bed or fluidised bed catalyst, particularly when the process according to the invention is carried out continuously.

The catalysts which were employed for carrying out the process according to the invention retain their activity and their selectivity over a long period of time, even when used several times or when the process according to the invention is carried out continuously, and give constantly high yields.

The amount of catalyst which is employed for carrying out the process according to the invention is in general from 0.1 to 2% by weight, preferably from 1 to 1.5% by weight, relative to the aniline used as the starting material. When a catalyst applied on a carrier is used, customarily from 1 to 20% by weight, preferably from 10 to 20% by weight, relative to the starting material, is employed.

The process according to the invention is carried out, if appropriate, in the presence of further inert organic solvents and/or diluents, and/or in the presence of water. Benzene, chlorobenzene, o-dichlorobenzene, toluene and xylene, preferably toluene, may be mentioned as examples of inert, organic solvents and/or diluents.

In general, the process according to the invention is carried out in an acid medium. The acid medium can be produced by the hydrogen halide formed in the reaction.

When the reaction takes place in the presence of water, the process according to the invention is carried out in general at a pH value of less than 4, preferably of less than 1.

To adjust the acid medium to a pH value of <1, a small amount of hydrogen chloride may be added to the mixture before the beginning of the reaction. The amount of hydrogen chloride added is preferably kept very small in order to avoid an increased inevitable production of hydrogen chloride, or salts thereof, during the working-up.

In a particular embodiment of the process, the adjustment of the acid medium is achieved by re-using a noble metal catalyst, optionally applied on a carrier, from a preceding reaction mixture, the catalyst being separated, before re-use, from the strongly acid reaction mixture of a proceeding batch, and being washed, if appropriate, with hot water or hot dilute hydrochloric acid.

The process according to the invention may be illustrated with reference to the following equation for the dechlorination of pentachloroaniline to give 3,5-dichloroaniline:

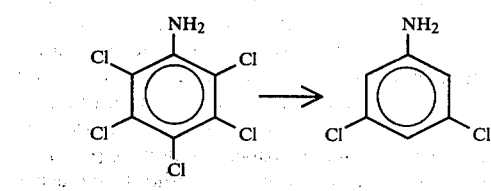

Using the process according to the invention, it is possible to use not only, for example, pure tetrachloroanilines or pentachloroanilines as starting materials, but also mixtures of tetrachloroanilines and pentachloroanilines as produced in the industrial production of tetrachlorobenzene by nitration and catalytic reduction of the nitro group.

Furthermore, instead of the chlorinated anilines, it is possible to employ the corresponding nitrochloro compounds as starting materials, and to carry out the reduction of the nitro group and the dehalogenation under conditions of hydrogenation in a one-pot reaction.

In general, the process according to the invention is carried out as follows: the starting material, the phenol, if appropriate a solvent or diluent, and the catalyst are initially introduced into an acid-resistant autoclave, for example an autoclave of enamel or tantalum, and, after the autoclave has been closed, the air is displaced by nitrogen and then the nitrogen with hydrogen.

To carry out the reaction, hydrogen gas is passed into the reaction mixture. In general, the reaction is carried out under a total pressure of from 5 to 100 bar, preferably under 10 to 60 bar, particularly preferably under 15 to 50 bar.

The process according to the invention is carried out in general at a temperature of from 100° to 250° C., preferably at 120° to 200° C., particularly preferably at 140° to 190° C.

The duration of the reaction depends, inter alia, on the reaction temperature employed and on the hydrogen pressure used, and is about 2 hours at 180° C.

After the end of the reaction, the mixture can be worked up in a manner which is in itself known. For example, after the mixture has been diluted with water, the catalyst can be separated off by filtering the hot mixture under suction. The anilines which are m-substituted by chlorine can then be liberated by the addition of, for example, alkali metal hydroxide solution, and can be extracted with a water-immiscible solvent, for example methylene chloride or toluene. The phenol remains in solution as the alkali metal phenolate. The halogenoanilines can be obtained from the solvent, for example, by distillation.

When a water-immiscible solvet and/or diluent is employed, the 3-chloro- or the 3,5-dichloroanilines can be liberated by the addition of aqueous alkali metal hydroxide. The organic solvent can then be separated off, and the aniline which is m-substituted by chlorine can be isolated therefrom, for example by distillation.

A particular form of the working-up may consist of the following: for example, after diluting the reaction mixture with water, filtering off the catalyst under suction and neutralizing the solution with, for example, sodium hydroxide solution, the organic phase is separated off, if necessary with the aid of an organic solvent, such as toluene, and the particular chlorine-substituted aniline is obtained by distillation.

The process according to the invention can be carried out both discontinuously and continuously.

The process according to the invention has the advantage that the selective dechlorination can be carried out to give a high yield under mild reaction conditions and at high concentrations of starting material, without the supplementary addition of salts, such as alkali metal or alkaline earth metal chlorides, and without the use of iodide or bromide ions, the recovery of which requires additional expense (see European Patent Application No. 0,015,219), and furthermore, without the use of heavy metal salts, such as those mentioned, for example, in European Patent Application No. 0,015,220.

A further advantage of the process according to the invention is that even chloroaniline mixtures which are difficult to separate, and which contain, in addition to the polychloroanilines which are substituted by chlorine in the m-position to the amino group, further chloroanilines or polychloroanilines in which there is no chlorine in the m-position to the amino group, can be used as a starting material. These compounds are dechlorinated by the process according to the invention to give aniline, which can readily be separated off by distillation. In contrast, the separation of a polychloroaniline mixture is inconvenient and tedious.

Further, by means of the process according to the invention, a mixture of tetrachloroanilines and pentachloroaniline, such as that obtainable from an industrially produced tetrachlorobenzene mixture by nitration and catalytic reduction of the nitro group, can be dehalogenated selectively and with a high yield to give 3,5-dichloroaniline.

Furthermore, it must be regarded as advantageous that the phenol employed in the dehalogenation reaction is not converted by hydrogen, under the reaction conditions mentioned and in the presence of noble metal catalysts, to give cyclohexanol or cyclohexanone by hydrogenation of the nucleus. In this process, the phenol can be recovered in each case by a simple separation operation, such as extraction or distillation, and can be re-used. The use of optionally substituted phenols in the process according to the invention provides yet another substantial advantage, since the compound to be dehalogenated can be employed in very high concentration, with a simultaneously low concentration of the noble metal catalyst. Particularly high space/time yields hitherto not achieved are obtained as a result.

The following may be mentioned as examples of anilines which are m-substituted by chlorine and of the formula (II), and which can be prepared by the process according to the invention: 3-chloroaniline, 3,5-dichloroaniline, 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorodiphenyl, 3-chloro-2-methoxyaniline, 5-chloro-2-methoxyaniline, 3,5-dichloro-2-methoxyaniline, 3-chloro-4-methoxyaniline, 5-chloro-3-methoxyaniline, 3,5-dichloro-4-methoxyaniline, 3-chloro-2-phenoxyaniline, 3,5-dichloro-2-phenoxyaniline, 3,5-dichloro-4-phenoxyaniline.

The 3-chloro- or 3,5-dichloroanilines obtainable by the process according to the invention are known intermediate products and can be used for the preparation of plant protection agents (German Patent Specification No. 1,034,912, German Offenlegungsschrift No. 2,021,327, German Offenlegungsschrift No. 1,812,206, German Offenlegungsschrift No. 1,958,183, U.S. Pat. Nos. 2,906,614, 2,655,445, and 3,652,737, German Offenlegungsschrift No. 2,905,780, German Offenlegungsschrift No. 2,207,576, German Offenlegungsschrift No. 2,324,591 and German Offenlegungsschrift No. 3,014,119).

The examples which follow are intended to illustrate the process according to the invention.

EXAMPLE 1

131 parts of a mixture of 2,3,4,5- and 2,3,5,6-tetrachloroaniline and pentachloroaniline in the ratio of 38:60:2 percent by weight and 200 parts of phenol are reacted with hydrogen over 20 parts of a 1% strength palladium/charcoal catalyst and a maximum pressure of 50 bar and at 170° C. in a tantalum autoclave, in the course of 10 hours, while stirring. After the autoclave has been cooled and the pressure released, the reaction mixture is diluted with 500 parts of water and separated off from the catalyst, and after the addition of toluene, the mixture is rendered alkaline with sodium hydroxide solution. The solution of 3,5-dichloroaniline in toluene, obtained by separation of the layers, is distilled. Yield: 90 g (=98%) of a 99% strength 3,5-dichloroaniline. The phenol can be recovered from the aqueous phase by acidifying the latter and extracting it by shaking with toluene. It was possible to re-use the catalyst 20 times without it losing any of its activity.

EXAMPLE 2

200 parts of phenol and 197 parts of a mixture of 2,3,4,5- and 2,3,5,6-tetrachloroaniline and pentachloroaniline in the ratio of about 38:60:2 percent by weight are reacted with hydrogen over 20 parts of a 1% strength palladium/charcoal catalyst under a maximum pressure of 50 bar and at 175° C. in a 0.85 l tantalum autoclave, in the course of 10 hours, while stirring. After the autoclave has been cooled and the pressure released, the reaction mixture is diluted with 800 parts of water and the catalyst is filtered off under suction from the hot solution and is re-used in a further reaction mixture after it has been washed with a little hot water. The solution of 3,5-dichloroaniline hydrochloride, phenol and water, which solution has been freed from the catalyst, is neutralised with sodium hydroxide solution. 3,5-Dichloroaniline and phenol are separated off from the aqueous phase with the aid of toluene, and the organic solution is distilled. A 98% strength 3,5-dichloroaniline is obtained in a yield of 95% with complete conversion of tetrachloroaniline and pentachloroaniline.

EXAMPLE 3

40 parts of 2,3,4,5-tetrachloroaniline, 150 parts of phenol and 12 g of a moist palladium/charcoal catalyst already used for this reaction (1% strength, 8 g dry) are mixed, and the mixture is stirred in a tantalum autoclave for 6 hours after forcing in hydrogen up to a total pressure of from 16 to a maximum of 18 bar at 165° C. After the pressurised vessel has been cooled and the pressure released, the reaction mixture is diluted with water, toluene is added, and the mixture is rendered alkaline with sodium hydroxide solution. The catalyst is separated off by filtering under suction. The toluene phase is distilled, and 27.7 parts (=99% of yield) of 98.5% strength 3,5-dichloroaniline are obtained.

EXAMPLE 4

A mixture of 200 parts of phenol, 150 parts of a tetrachloronitrobenzene/pentachloronitrobenzene mixture and 20 g of a 1% strength palladium/charcoal catalyst is first reduced with hydrogen at from 60° to 70° C. and under 10 bar in a tantalum autoclave, in the course of 6 hours, while stirring. Thereafter, the temperature is increased to 170° C. and the dehalogenation is carried out under a maximum total pressure of 50 bar in the course of 8 hours, while stirring further. After the reaction mixture has been worked up, 86 parts of 3,5-dichloroaniline are obtained by distillation. 94% yield.

EXAMPLE 5

In a tantalum autoclave, 81 parts of 99.1% strength 2,3-dichloroaniline and 180 parts of phenol are mixed with 25 parts of a palladium/charcoal catalyst (1% strength, 20 g dry) moistened with hydrochloric acid, and the mixture is reacted with hydrogen under a maximum total pressure of 50 bar at 175° C., in the course of 4 hours, while stirring. After the pressurized vessel has been cooled and the pressure released, the mixture is diluted with 400 parts of water and 200 parts of concentrated aqueous sodium hydroxide solution, and after the addition of 200 parts of toluene, the mixture is warmed to 90° C. The catalyst is filtered off under suction and rinsed out with hot toluene. The combined toluene solutions are distilled, 60.5 parts of 3-chloroaniline (=96% of theory) being obtained.

EXAMPLE 6

61.5 parts of 2,3,5,6-tetrachloro-4-methylaniline, 180 parts of phenol and 15 parts of a 1% strength palladium/charcoal catalyst are reacted with hydrogen under a maximum pressure of 50 bar at 180° C. in a tantalum autoclave, in the presence of a small amount of hydrochloric acid, in the course of 5 hours, while stirring. After the pressurized vessel has been cooled and the pressure released, the mixture is diluted with 300 parts of water and 200 parts of toluene, rendered alkaline, heated to 90°, and separated from the catalyst. The catalyst is boiled up with toluene, and the combined toluene solutions are distilled. 44 parts of 3,5-dichloro-4-methylaniline, bp. 146°–155°/18 mbar, 98% strength, are obtained; yield: 98% of theory.

EXAMPLE 7

131 parts of a tetrachloroaniline/pentachloroaniline isomer mixture (according to Example 2), 200 parts of o-cresol and 20 parts of a Pd/charcoal catalyst (1% strength) and 5 parts of concentrated hydrochloric acid are reacted with hydrogen at 175° C. and under 50 bar in a tantalum autoclave, in the course of 10 hours. After the autoclave has been cooled and the pressure released, the mixture is rendered alkaline with 200 parts of toluene, 400 parts of water and 250 parts of aqueous concentrated sodium hydroxide solution, and is heated to the boil, and thereafter the catalyst is separated off by filtering under suction. After extracting the aqueous alkaline phase by shaking with toluene, the toluene solutions of 3,5-dichloroaniline are distilled. 85 parts of a 98% strength 3,5-dichloroaniline, bp. 130°–136°/18 mbar, are obtained.

What is claimed is:

1. In a process for the preparation of an aniline which is m-substituted by chlorine by the selected dehalogenation of a more highly halogenated aniline of the formula

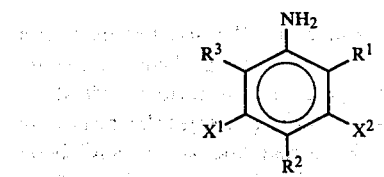

wherein
$X^1$ and $X^2$ are identical or different and represent chlorine, hydrogen or an optionally substituted alkyl, aryl, aralkyl, alkoxy or aralkoxy radical, one of the radicals $X^1$ and $X^2$ representing chlorine in the preparation of 3-chloroaniline, and $X^1$ and $X^2$ representing chlorine in the preparation of 3,5-dichloroaniline; and $R^1$, $R^2$, or $R^3$ are identical or different and represent chlorine, hydrogen or an optionally substituted alkyl, aryl, aralkyl, alkoxy or aryloxy radical, at least one of the radicals $R^1$, $R^2$, or $R^3$ representing chlorine, with hydrogen in an acid medium in the presence of a noble metal, in elementary or bonded form, at an elevated temperature and pressure, the improvement which comprises carrying out the process in the presence of an optionally substituted phenol and in the absence of an iodine compound.

2. A process according to claim 1, wherein said optionally substituted phenol is one mono-substituted or poly-substituted by an alkyl group having up to 4 carbon atoms and/or by a halogen.

3. A process according to claim 1, wherein said optionally substituted phenol is selected from the group consisting of phenol, ortho cresol, meta cresol, para cresol, 2,3-xylenol, 2,4-xylenol, 2,5-xylenol, 2,6-xylenol and mixtures thereof.

4. A process according to claim 1, wherein said optionally substituted phenol is selected from the group consisting of phenol, a mixture of ortho-, meta- and para-cresol and a mixture of meta- and para-cresol.

5. A process according to claim 1, wherein said optionally substituted phenol is employed in an amount from 1 to 90% by weight, based upon the total weight of the reaction mixture.

6. A process according to claim 1, wherein said optionally substituted phenol is employed in an amount from 30 to 70% by weight, based upon the weight of the reaction mixture.

7. A process according to claim 1, wherein said noble metal catalyst is disposed on a carrier and following the reaction is reused in a subsequent reaction mixture either directly or after washing with water or hydrochloric acid.

8. A process according to claim 1, wherein said aniline is one of the formula

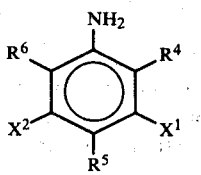
(II)

wherein
X[1] and X[2] are identical or different and representing chlorine, hydrogen, or an optionally substituted alkyl, aryl, aralkyl, alkoxy or aryloxy radical, one of the radicals X[1] or X[2] representing chlorine in the preparation of 3-chloroaniline, and X[1] and X[2] representing chlorine in the preparation of 3,5-dichloroaniline, and R[4] and R[5] and R[6] are identical or different and represent hydrogen or an optionally substituted alkyl, aryl, aralkyl, alkoxy or aryloxy radical.

9. A process according to claim 1, wherein said aniline is one of the formula

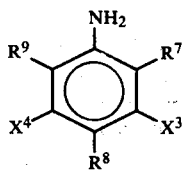
(III)

wherein
X[3] and X[4] are identical or different and represent chlorine or hydrogen, one of the radicals X[3] or X[4] representing chlorine in the preparation of 3-chloroanilines, and
X[3] and X[4] representing chlorine in the preparation of 3,5-dichloroanilines,
R[7], R[8] and R[9] are identical or different and represent hydrogen, the methyl group or the phenyl group, or the radical

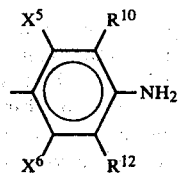

or,

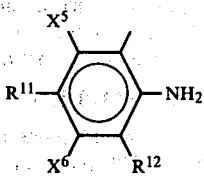

wherein
X[5] and X[6] are identical or different and represent chlorine or hydrogen, and
R[10], R[11], R[12] are identical or different and represent chlorine, hydrogen, the methyl group or the phenyl group, at least one of the radicals R[7], R[8] or R[9] representing chlorine.

10. A process according to claim 1, wherein the process is carried out in the absence of a bromine compound.

* * * * *